(12) United States Patent
Messina

(10) Patent No.: US 6,383,508 B1
(45) Date of Patent: May 7, 2002

(54) ANIMAL REPELLENT AND METHOD

(76) Inventor: James Messina, 58 Califon Rd., Long Valley, NJ (US) 07853

( * ) Notice: Subject to any disclaimer, the term of this patent is extended or adjusted under 35 U.S.C. 154(b) by 0 days.

(21) Appl. No.: 09/783,625

(22) Filed: Feb. 14, 2001

(51) Int. Cl.[7] .............................................. A01N 25/34
(52) U.S. Cl. ...................... 424/411; 424/405; 424/406; 424/407; 424/418; 424/421; 514/920
(58) Field of Search .................. 424/411, 406, 424/405, 407, 418, 421; 514/920

(56) References Cited

U.S. PATENT DOCUMENTS 4,536,583 A * 8/1985 Mookherjee et al.
5,368,866 A * 11/1994 Loucas
5,783,204 A * 7/1998 Messina

OTHER PUBLICATIONS

Schilcher, Dtsch. Apoth. Ztg. (124, No. 29, 1433–42, 1984).*

* cited by examiner

*Primary Examiner*—Jean C. Witz
*Assistant Examiner*—Brett Ozga
(74) *Attorney, Agent, or Firm*—Graham, Curtin & Sheridan; Richard T. Laughlin, Esq.

(57) ABSTRACT

A deer and geese repellent formulation and method for warding off geese or deer from a shrub or plant. The formulation is an admixture of water, Rosemary oil emulsion, mint oil emulsion, a thickener, white distilled vinegar and dried eggs. The formulation can be applied to a support medium, such as clay or a length of rope, and then associated with the vegetation to be protected. The formulation can also be formed into a viscous composition and used in containers near the vegetation to be protected.

10 Claims, No Drawings

ANIMAL REPELLENT AND METHOD

The invention generally relates to an animal repellent and, in particular, the invention relates to a repellent composition which is transparent and can be applied to a wide range of surfaces, and to a method for the use of such a composition.

BACKGROUND OF THE INVENTION

The prior art deer repellent formulation is described in U.S. Pat. No. 4,965,070, issued Oct. 23, 1990, to James Messina, the same inventor as this application. The prior art formulation consisted essentially of, by volume, 68 to 90% water; 6 to 10% thiram; 0.5 to 2% chicken eggs; 1 to 2% liquid hot sauce; 2 to 16% adhesive to aid in adhering to vegetation; and 0.5 to 2% coloring dye. The dye is necessary so the coating will blend in with the foliage.

One problem of the prior art deer repellent formulation is that, although the ingredients are common materials, it requires approval of the Environmental Protection Agency ("EPA") which involves long and costly tests. Formulations of this type are applied by small companies, such as landscape gardeners, and the obtaining of approval from the EPA is financially prohibitive. This results in widespread destruction of homeowners' landscaping because of the unfettered proliferation of deer in suburban areas. Further, the prior art materials have a limited effective life and the odor of the formulation can limit its acceptance. A further problem with the prior art compositions is that they require a colorant to hide their presence on the foliage.

OBJECTS OF THE INVENTION

One object of the present invention is to provide an improved animal repellent formulation for application to shrubs, plants or the like, which can be acceptable under EPA regulations.

Another object of the invention is to provide an animal repellent formulation more acceptable to humans.

Another object of the invention is to make use of EPA-approved components without reduction of the effectiveness of the treatment.

A still further object is to provide such a composition which is transparent.

Other objects and the advantages of the invention will appear from the following description.

SUMMARY OF THE INVENTION

According to the present invention, an animal repellent formulation and method for its use are provided. The formulation is an aqueous solution or mixture consisting essentially of water and a composition comprising 5 to 20 ounces of Rosemary oil emulsion, 5 to 20 ounces of mint oil emulsion, zanthan gum as a thickener and sufficient water to make one gallon (128 ounces). If desired, the formulation can be modified by adding 10 to 30 ounces of white distilled vinegar, 10 to 30 ounces of dried eggs and 1 to 15 teaspoons of table salt. The thickener can be added to give the composition the desired application characteristics. Typical would be 1 to 5% of the total composition of thickener. All of the percentages are by volume of the composition.

Prior to application to vegetation, the composition is diluted in a concentration of one part of repellent to approximately 5 to 15 parts water. The mixture is stirred until a uniform composition is obtained. The composition is then diluted, one (1) part composition with nine (9) parts water, and is sprayed onto the foliage of plants or grass to be protected using a fine nozzle power spray at the rate of approximately one gallon of composition for each 35,000 square feet of foliage.

This formulation has proved effective in repelling deer and geese.

As an alternate procedure, the composition can be impregnated into a rope with the rope being placed around the vegetation to be protected.

DESCRIPTION OF THE PREFERRED EMBODIMENT

The preferred animal repellent formulation is an aqueous solution or mixture consisting essentially of water and a composition comprising 10 ounces of Rosemary oil emulsion, 10 ounces of mint oil emulsion, zanthan gum as a thickener and sufficient water to make one gallon (128 ounces). If desired, the formulation can be modified by adding 20 ounces of white distilled vinegar, 20 ounces of dried eggs and 10 teaspoons of table salt. In certain instances, when weather conditions are dry, a preservative such as potassium sorbate can be used. The thickener can be added to give the composition the desired application characteristics. Typical would be 1 to 5% of the total composition of thickener. All of the percentages are by volume of the composition. In some instances where greater adherence to the foliage is desired, a sticker such as the material sold under the trademark "Nu Film P" can be added. As an alternative, "CLEARSPRAY" or the like can be used. In particular, the adhesive is used for an animal repellent assembly, which is exposed to substantial amounts of rain or snow.

The composition of the invention can be utilized in the manner described in U.S. Pat. No. 5,183,661, issued on Feb. 2, 1993 to James Messina, the same inventor as in this application. The formulation of the invention can be applied to a support medium such as a solid braid, number 8, cotton and polyester, one-quarter inch diameter, sash cord rope of 100-foot length, which is sold by the Lehigh Group, Allentown, Pa. 18105, USA. The support medium can also be a clay material, which ranges in size of clay granules or particles, from dustless fine granules to about one-quarter inch overall diameter or thickness granules. The clay material comes packaged in a0.20 pound bag, which is made of a finely woven cloth material and which has a drawstring along an open top edge thereof, and which has a size of about 4 inches in height by about 3 inches in width when flat. The drawstring threads through spaced holes located about one-half inch down from the bag top edge.

The animal repellent assembly of support rope and formulation can be wrapped around a shrub or plant or strung between shrubs and plants. The animal repellent assembly of support medium clay material and formulation can be distributed under and around shrubs and plants or the like.

It is noted that 16 fluid ounces of animal repellent formulation is sufficient to wet the 100-foot length of one-quarter inch diameter rope. Also, 11 fluid ounces of animal repellent formulation is sufficient to wet throughout the one pound of clay granules. A shorter rope length requires proportionally less fluid ounces of formulation based upon rope length and rope cross-section areas. Less than one pound of clay granules medium requires proportionally less fluid ounces of formulation based upon medium volume.

The animal repellent formulation can also be prepared for addition to a container having sufficient holes or openings to allow the animal to lick the container and come in contact with the repellent formulation. The fluid animal repellent formulation is admixed with wheat flour and corncob grounds to form a semi-solid composition and then poured into the container having openings.

The following examples are given for purposes of illustration and not by way of limitation.

EXAMPLE 1

An animal repellent formulation in the preferred embodiment for outdoor application as follows:

10 ounces of Rosemary oil emulsion;

10 ounces of mint oil emulsion.

Water is added to make one gallon of mixture to make a concentrate which can be diluted with water on the job site and applied to the foliage in a fine mist from a power spray.

EXAMPLE 2

The animal repellent formulation of Example 1 can have added:

20 ounces of white distilled vinegar;

10 ounces of table salt;

20 ounces of dried chicken eggs.

EXAMPLE 3

The animal repellent formulation of Example 2 with the addition of potassium sorbate as a preservative.

EXAMPLE 4

The animal repellent formulation of Example 2 with the addition of 1 to 10 ounce of zanthan gum as a thickener.

EXAMPLE 5

The animal repellent formulation of Example 2 with the addition of 5 ounces of "Nu-Film P" as a sticker to aid in the adherence of the formulation to the foliage.

EXAMPLE 6

The composition of Example 2 is formed into a solid medium by mixing the following:

2 cups of wheat flour;

2 cups of ground up corncobs;

2 cups of the formula of Example 2.

The composition is mixed uniformly and then added to a container with holes. The size of the container is 1 inch in diameter by 2 inches in length. The container is hung or tied to the plant to be protected or elevated on a post adjacent to the plant.

EXAMPLE 7

The animal repellent composition of Example 2 is utilized as follows:

a 100-foot length of support rope of one-quarter inch diameter, and of cotton and polyester, solid braid material;

16 fluid ounces of animal repellent formulation of Example 2 is placed in a container. The animal repellent formulation is distributed evenly along the support rope length by dipping the rope into the container.

EXAMPLE 8

The animal repellent formulation of Example 1 is admixed as follows:

one pound by weight of clay granules in a particle size distribution from dustless fine particles to about one-quarter inch overall thickness particles for a support medium; eleven fluid ounces of animal repellent formulation of Example 1.

The animal repellent formulation is mixed with the support medium clay granules.

While the invention has been described in its preferred embodiment, it is to be understood that the words which have been used are words of description rather than limitation, and that changes may be made within the purview of the appended claims without departing from the true scope and spirit of the invention in its broader aspects.

What is claimed is:

1. A repellent for deer and geese concentrate formulation consisting essentially of an aqueous solution or mixture containing 5 to 20 ounces of Rosemary oil emulsion, 5 to 20 ounces of mint oil emulsion, 10 to 30 ounces of white distilled vinegar and 10 to 30 ounces of dried eggs, and sufficient water to make approximately one gallon of concentrate.

2. The animal repellent formulation as defined in claim 1 with the addition of 1 to 15 teaspoons of table salt.

3. The animal repellent composition comprising the formulation as defined in claim 1 wherein 16 fluid ounces of the formulation is carried by a 100-foot length of support rope of one-quarter inch diameter and made of cotton and polyester solid braid material.

4. The animal repellent composition as defined in claim 3 wherein the rope is a selected length and selected size diameter of a material like to cotton and polyester solid braid material and the rope has a selected volume of animal repellent formulation based upon about 16 fluid ounces of formulation per 0.20 square inch section area and per 100-foot length of support rope, said formulation being about evenly distributed along the length of the support rope.

5. The animal repellent composition as defined in claim 1 and one pound by weight of clay granules in a particle size distribution from about dustless fine particles to about one-quarter inch overall thickness particles for a support medium and an adhesive in a quantity sufficient for adherence to the support medium; said formulation being about evenly distributed throughout the support medium clay granules.

6. An animal repellent composition as defined in claim 1 further comprising:

a selected weight of support medium clay particles in a particle size distribution from about dustless fine particles to about one-quarter inch overall thickness particles;

a selected volume of animal repellent formulation based upon about 11 fluid ounces of formulation per pound weight of support medium clay granules consisting of about 10 fluid ounces of water prior to any evaporation of the water, said formulation being about evenly distributed throughout the support medium clay particles.

7. A method of repelling an animal from a shrub or plant including the steps of:

preparing a animal repellent formulation by admixing about 15 fluid ounces of water, about 0.125 ounces by weight of dried chicken eggs 1.5 ounces of Rosemary oil emulsion, 1.5 ounces of mint oil emulsion, 2.5 ounces of white distilled vinegar and an adhesive;

forming a support medium for the formulation;

distributing the formulation evenly on the support medium; and disposing the support medium on and about the shrub or plant.

8. The method of claim 7, wherein the support medium is a braided rope of about one-quarter inch diameter.

9. The method of claim 8, wherein the support medium is a volume of clay granules having a particle size distribution from dustless fine particles to about one-quarter inch thickness particles.

10. The method of forming a animal repellent material which comprises mixing wheat flour with finely ground corncobs, adding a mixture of Rosemary oil emulsion, mint oil emulsion and a thickener, blending the mixture and placing in a ventilated container and the placing the container in the vicinity of the foliage to be protected.

* * * * *